(12) United States Patent
Komuro

(10) Patent No.: US 8,104,482 B2
(45) Date of Patent: Jan. 31, 2012

(54) METHOD FOR TREATING A THROMBOSIS

(76) Inventor: Toshio Komuro, Tokyo (JP)

(*) Notice: Subject to any disclaimer, the term of this patent is extended or adjusted under 35 U.S.C. 154(b) by 1130 days.

(21) Appl. No.: 11/502,081

(22) Filed: Aug. 10, 2006

(65) Prior Publication Data

US 2006/0275348 A1  Dec. 7, 2006

Related U.S. Application Data

(62) Division of application No. 10/492,341, filed as application No. PCT/JP03/07110 on Jun. 5, 2003, now abandoned.

(30) Foreign Application Priority Data

Jun. 5, 2002 (JP) .................................. 2002-163695

(51) Int. Cl.
*A61K 9/70* (2006.01)
(52) U.S. Cl. .................... 128/898; 424/443; 428/402
(58) Field of Classification Search .................. 424/443; 428/402; 128/898
See application file for complete search history.

(56) References Cited

U.S. PATENT DOCUMENTS

| | | | |
|---|---|---|---|
| 4,243,592 A * | 1/1981 | Morton, Jr. .................... | 549/373 |
| 5,258,228 A | 11/1993 | Komuro | |
| 5,532,253 A * | 7/1996 | Fujioka et al. .................. | 514/312 |
| 5,779,950 A | 7/1998 | Kang | |
| 7,207,959 B1 * | 4/2007 | Chandran ...................... | 601/149 |
| 7,241,316 B2 * | 7/2007 | Evans et al. ................. | 623/23.51 |
| 2002/0032173 A1 * | 3/2002 | Saito et al. ...................... | 514/62 |
| 2003/0037784 A1 * | 2/2003 | Lurie ........................ | 128/202.28 |
| 2004/0034434 A1 * | 2/2004 | Evans et al. ................. | 623/23.51 |
| 2004/0225049 A1 | 11/2004 | Komuro | |

FOREIGN PATENT DOCUMENTS

| | | |
|---|---|---|
| EP | 0 462 275 A1 | 12/1991 |
| EP | 1 291 405 A1 | 3/2003 |
| JP | 62-184088 A | 8/1987 |
| JP | 3-190990 A | 8/1991 |
| JP | 3-241025 A | 10/1991 |
| JP | 3-250087 A | 11/1991 |
| JP | 4-73226 A | 3/1992 |
| JP | 2001-191318 A | 7/2001 |
| JP | 2001-199758 A | 7/2001 |
| WO | 01/88054 A1 | 11/2001 |

* cited by examiner

*Primary Examiner* — Henry M Johnson, III
*Assistant Examiner* — Jeffrey Lipitz
(74) *Attorney, Agent, or Firm* — Holtz, Holtz, Goodman & Chick PC

(57) ABSTRACT

A method for treating or preventing a thrombosis in a person in need thereof comprising disposing in or on an article an effective antithrombotic amount of a composition and providing the article to be in close proximity to the skin of the person, the composition comprising (i) alumina, (ii) at least one substance selected from the group consisting of silica and titanium oxide and (iii) at least one element or compound selected from the group consisting of platinum, a platinum compound, palladium, a palladium compound, iridium, an iridium compound, rhodium and a rhodium compound.

8 Claims, No Drawings

METHOD FOR TREATING A THROMBOSIS

CROSS-REFERENCE TO RELATED APPLICATIONS

This application is a Divisional application of application Ser. No. 10/492,341 filed Apr. 9, 2004 (abandoned), which is the United States national phase application of International application PCT/JP03/07110 filed Jun. 5, 2003.

TECHNICAL FIELD

The present invention relates to a platinum-containing ceramic composition having antithrombotic properties. More specifically, the present invention relates to a antithrombotic composition comprising alumina, one or more types of substances selected from silica or titanium oxide, and one or more types of substances selected from platinum, palladium, iridium, rhodium or a compound thereof, as well as antithrombotic articles containing that composition.

BACKGROUND ART

In recent years, increasing attention has been focused on ceramics containing platinum as far infrared ray radiating materials. Far infrared rays are electromagnetic waves that have a radiation/emission wavelength of several to 400 μm, and demonstrate superior heating and drying effects. Consequently, ceramics as far infrared radiating materials have been used in the field of high-quality food processing since they are capable of heating uniformly to the interior without excessively heating the surface. In addition, fibers having far infrared ray effects, in which far infrared ray radiating materials are blended into fibers or coated on the surface, are widely used in bedding, clothing, undergarments and so forth.

For example, Japanese Provisional Patent Publication No. 184088/1987 describes that a powder for-radiating far infrared rays that contains alumina, silica and platina has the effect of aging and improving shelf life and flavor of food products.

Japanese Provisional Patent Publication No. 190990/1991 describes that a powder for radiating weak infrared energy that contains alumina, titanium and platina has the effect of aging and improving shelf life and flavor of food products, that synthetic fibers containing this powder promote blood circulation, have heating effects and are effective against poor circulation and symptoms of arthritis.

In addition, Japanese Provisional Patent Publication No. 241025/1991 and Japanese Provisional Patent Publication No. 73226/1992 describe that a textile produced from threads obtained by mixing a powder for radiating far infrared rays composed of alumina, silica and platina with Nylon or polyester demonstrates extremely satisfactory warmth retaining properties for the body.

As has been described above, although ceramic compositions containing platinum are known to have circulation promoting action, heating action and warmth retaining action on the body and be effective against poor circulation and arthritis, there is a need to use such compositions in other applications.

Thus, an object of the present invention is to discover a novel application for a ceramic composition containing platinum.

DISCLOSURE OF THE INVENTION

As a result of conducting extensive studies on a ceramic composition containing platinum, the inventors of the present invention found that this composition demonstrates an effect that prevents the formation of thrombus, namely antithrombotic properties, by having this composition present in close proximity to skin of the body, thereby leading to completion of the present invention.

The present invention provides an antithrombotic composition comprising: (i) alumina, (ii) at least one substance selected from silica and titanium oxide, and (iii) at least one element or compound selected from platinum or a platinum compound, palladium or a palladium compound, iridium or an iridium compound and rhodium or a rhodium compound.

The present invention also relates to the above antithrombotic composition additionally comprising: (iv) at least one element or compound selected from silver or a silver compound or gold or a gold compound.

In addition, the present invention relates to antithrombotic articles that contain the above antithrombotic composition, and particularly clothing and bedding.

BEST MODE FOR CARRYING OUT THE INVENTION

The alumina ($Al_2O_3$) of component (i) contained in the composition of the present invention preferably uses high-purity alumina (aluminum oxide) having a purity of 99.9% or higher and superior sintering. Commercially available, powdered high-purity alumina can be used for the alumina. The content of component (i) is preferably 20-60 parts by weight, and more preferably 30-50 parts by weight. In addition, although the particle diameter of component (i) depends on the product that uses the composition of the present invention and its mode, the component having a normal particle diameter, for example, several μm or less can be used. In the case of using by mixing into fibers, the particle diameter of component (i) is preferably adjusted depending on the diameter of the fibers, and is normally 2 μm or less, preferably 1.5 μm or less, more preferably 1.0 μm or less, for example, a particle diameter of about 0.3 μm.

The silica ($SiO_2$) of component (ii) contained in the composition of the present invention is preferably high-purity silica having a purity not less than 99.8%, and for example., commercially available microparticulate anhydrous silica may be used. The particle diameter of the silica is the same as that of component (i).

The purity, particle diameter and blended amount of the titanium oxide ($TiO_2$) of component (ii) contained in the composition of the present invention are the same as those of the previously mentioned component (ii). Commercially available microparticulate titanium oxide may be used. In addition, high-purity, hyperfine titanium dioxide, obtained by granulating and purifying from coarse particles of titanium dioxide having a purity of 80% or higher, may also be used.

Component (ii) consisting of one or more types of compounds selected from silica and titanium oxide is contained in the composition of the present invention at preferably 40-80 parts by weight, and more preferably 50-70 parts by weight.

Titanium oxide is preferably used for component (ii) in the antithrombotic composition of the present invention.

At least one type of element or compound thereof selected from platinum or a platinum compound, palladium or a palladium compound, iridium or an iridium compound and rhodium or a rhodium compound of component (iii) contained in the composition of the present invention is preferably added in the form of a colloid. This is because so-called colloidal activation can be expected that results in the adsorption of oxygen and hydrogen. Platinum or a platinum compound is preferably used for component (iii). Component (iii) is contained as metal in the composition of the present invention preferably at 0.0005-0.010 parts by weight, and more preferably at 0.001-0.004 parts by weight. In addition, a dispersed colloid of component (iii) (to be referred to as a component (iii) colloid), in which component (iii) is dispersed in the form of a colloid in, for example, a hydrochloric acid solution at a particle diameter of about 0.7-4 nm (7-40 Å), is preferably used for component (iii). Component (iii) is used by being contained in a colloid at 0.1-5% by weight, preferably 0.5-2% by weight and more preferably 0.8-1.2% by weight, and in consideration of the concentration of component (iii) in the colloid, component (iii) is added so as to be contained at 0.0005-0.010 parts by weight in the composition. Furthermore, ordinary methods can be used for preparing the component (iii) colloid. For example, a commercially available platinum colloidal solution containing 1% by weight of platinum may be used.

The silver or silver compound or gold or gold compound of component (iv) arbitrarily used in the composition of the present invention is preferably used in the form of a powder, and a commercially available silver powder may be used. Component (iv) is contained as silver in the composition of the present invention at 0-10 parts by weight, preferably 0.5-5 parts by weight, and more preferably 0.7-2.0 parts by weight.

In addition, the composition of the present invention may also contain silicon nitride. Silicon nitride enhances the action of hydrogen, and is thought to fulfill the role of restricting the direction of movement of hydrogen ions to a specific direction. However, in the case. silicon nitride is contained, it is preferably contained in an amount of 3 parts by weight or less.

The antithrombotic composition of the present invention can be produced by mixing one or more types of substances selected from alumina, silica and titanium oxide with platinum or platinum oxide respectively dispersed in a colloid, loading the platinum on each of the particles, mixing the particles loaded with platinum by stirring, and as necessary, also mixing in a powder of silver, gold or compound thereof. In addition, the antithrombotic composition of the present invention can also be produced by adding a predetermined amount of platinum colloid into a predetermined amount of alumina particles only, adding silica and/or titanium oxide to the alumina loaded with platinum, mixing by stirring, adding silver powder and again mixing by stirring.

Moreover, the composition of the present invention can be produced by mixing platinum colloid with a powder raw material composed of one or more types of the previously mentioned component (i), component (ii) and component (iv) which is an arbitrary component, diluting with a solvent and so forth until it has a desired sprayable fluidity, and heating for about 10 minutes to 1 hour at about 50-150° C. after spraying. Any solvent can be used for the diluting solvent provided it does not inhibit the effects of the composition of the present invention, examples of which include pure water and alcohol. A known dispersant may be added to improve dispersivity.

The antithrombotic composition of the present invention can be produced in the form of a fine particulate powder having a particle diameter of 0.1-2.0 μm, and preferably. 0.2-1.0 μm.

The present invention also relates to an antithrombotic article containing the antithrombotic composition described above. Examples of articles include clothing such as undergarments. (such as underpants, tights, stockings and hosiery), sleepwear (such as pajamas, sleeping robes and negligees), Western style clothing (such as sweaters, shirts, trousers, skirts and blouses), Oriental clothing (such as kimonos, vests and long shirts) and aprons, bedding such as futons, futon covers, blankets, sheets, mattress pads, pillows, pillow covers and mattresses, accessories such as socks, hats, neckties, handkerchiefs and waist bands, footwear such as shoes, floor coverings such as carpeting, curtains, and furniture such as beds and chairs, with clothing and bedding being. particularly preferable examples.

An antithrombotic article of the present invention can be produced by, for example, blending the antithrombotic composition into the article material or adhering to the surface of the article.

For example, in order to blend the antithrombotic composition into the fibers of bedding or sleepwear materials, a method can be employed in which 0.1-25% by weight, preferably 0.1-3% by weight, and more preferably 0.3-1.5% by weight of the antithrombotic composition is mixed into a synthetic polymer material of the fiber material; this mixture is then spun into filaments or hollow fibers and so forth using a commonly employed spinning method such as the melting method to obtain a thread; textiles and knits are produced from the resulting threads; and these can then be used to produce bedding and sleepwear such as futons, sheets, blankets, mattress pads, pillows, pillow covers, shirts, trousers and pajamas using conventional methods. Various types of textiles, bedding and sleepwear can also be obtained by blending threads containing the composition of the present invention obtained in the manner described above with other threads not containing the composition of the present invention, such as cotton, hemp, silk, wool and other natural fibers or synthetic fibers.

In addition, the antithrombotic composition of the present invention can also be blended into an article material by mixing the antithrombotic composition of the invention into a synthetic resin material and producing molded products of any desired shape such as sphere-like, oval-like, cylinder-like, plate-like, laminate-like or pipe-like, and then, for example, using the resulting pipes as the filling material of a pillow.

In order to adhere the antithrombotic composition to an article, a method can be employed in which a mixture consisting of the antithrombotic composition and a synthetic polymer material is sprayed, coated to the article, or the article is dipped into the mixture.

Here, the synthetic polymer materials include Nylon, Vinylon, esters, acryls, urethanes, polyamides, polyesters, polyacrylonitriles, polyolefins and acetates.

In the production of an article of the present invention, various types of additives may be blended as necessary, examples of which include catalysts such as magnesium oxide, mica, calcium carbonate and zeolite, plasticizers, UV absorbers, fillers, colorants, coloring preventives, flame retardants, anti-bleeding agents, stabilizers, heat resistance agents and fluorescent whiteners.

An article obtained by the above method, particularly the method in which the antithrombotic composition is blended into an article material, is able to prevent a decrease in the content of antithrombotic composition since each component of the antithrombotic composition is firmly adhered within the fibers or molded article. In addition, the content of the composition of the present invention can be increased by such methods as compared with conventional methods.

Examples of materials that can be used as bedding materials of the present invention include threads (such as filaments and staples), hollow fibers, textiles, knits, non-woven fabrics and any desirable shaped molded products (such as sphere-like, oval-like, cylinder-like, plate-like, laminate-like and pipe-like) containing the antithrombotic composition of the present invention.

EXAMPLES

The examples shown below indicate typical embodiments, but do not limit the scope of the present invention.

Example 1

Production of Antithrombotic Composition (1)

Commercially available alumina, silica and titanium oxide (titania) were adjusted in particle size to a particle size of 1 μm or less each. Next, 0.083 parts by weight aliquots (namely, containing 0.0008 parts by weight of platinum each) of a platinum colloid solution containing 1% platinum (Tanaka. Precious Metals Co. Ltd., particle diameter: 40 Angstroms) were separately mixed with 33 parts by weight aliquots of each particle to prepare a colloidal mixture. Next, 1.0 parts by weight of silver powder (Tanaka Precious Metals Co. Ltd.), having a particle diameter ranging from 0.2-1.0 µm and an average particle diameter of 0.7 µm, were added to 99.25 parts by weight of this mixture. Thus, the blending ratio of each substance in the composition of the present example was 33.0025% by weight of alumina, 33.0025% by weight of silica, 33.0025% by weight of titanium oxide, 0.0025% by weight of platinum and 0.99% by weight of silver.

Example 2

Production of Antithrombotic Composition (2)

A composition was formed in the same manner as Example 1 with the exception of changing the content of the composition to 49.499% by weight of alumina, 49.499% by weight of titanium oxide (titania), 0.002% by weight of platinum and 1.0% by weight of silver. The resulting composition was diluted with pure water until it had a fluidity that allowed it to be sprayed, after which it was sprayed and uniformly dispersed and then heated for 10 minutes to 1 hour at about 50-150° C. to produce a composition in the form of a fine particulate powder.

Example 3

Production Method of Antithrombotic Fibers

5% by weight of the composition obtained in Example 2 was mixed into polyester chips to produce a master batch. 10% by weight of this master batch was then mixed into polyester during fiber spinning to produce antithrombotic fibers (polyester). Thus, the proportion of antithrombotic composition in the polyester fibers was 0.5% by weight. In addition, the produced fibers were I: long fibers (filaments) of 75 denier and 72 filament and II: short fibers (staples) of 6 denier and 51 mm hollow fiber.

Example 4

Production of Antithrombotic Pipes

5% by weight of the composition obtained in Example 2 was mixed into polyethylene chips to produce a master batch. 10% by weight of this master batch was then mixed in during the production of polyethylene pipes. Thus, the proportion of antithrombotic composition in the pipes was 0.5% by weight. In addition, the resulting pipes had a diameter (outer diameter) of 5 mm and length of 7 mm.

Example 5

Production of Various Antithrombotic Bedding and Sleepwear

The following bedding and sleepwear were produced in accordance with ordinary methods from the fibers and pipes obtained in Examples 3 and 4.
(1) Sheets
　Form: Flat type, 150 cm wide×230 cm long
　Fiber blending ratio: 100% antithrombotic fibers (polyester)
　other: Plain fabric (100% antithrombotic fibers for warp and weft)
(2) Blanket
　Form: Double-sided raised fibers, 140 cm wide×200 cm long
　Fiber blending ratio: Raised fibers—50% antithrombotic fibers (polyester), 50% cotton
　Other: Raised fibers—two ply blended yarn of No. 40 cotton used for the antithrombotic fibers (polyester)
(3) Mattress Pad
　Form: 90 cm wide×185 cm long×2 cm thick, weight: 1.5 kg
　Fiber blending ratio:
　　Filling—100% antithrombotic fibers (polyester)
　　Siding—100% antithrombotic fiber fabric (polyester)
　Other: Quilting finished
(4) Pillow
　Form: Five-section filled (pipes), fine adjustment type, 60 cm wide×50 cm high (overall)
　Components:
　　Filler—100% antithrombotic pipes (polyethylene)
　　Body case—100% cotton
　　Body cover—100% cotton
　Other: As a result of dividing the pillow into five mesh pouches and filling them with filler, a structure results in which the location where the head is placed can be finely adjusted. In addition, the five mesh pouches are adhered to the body cover, thereby resulting in a structure that supports the neck and shoulders.
(5) Shirt
　Form: Crew neck, long sleeve
　Fiber blending ratio: 97% antithrombotic fibers (polyester), 3% polyurethane fabric
(6) Trousers
　Form: Long trousers
　Fiber blending ratio: 97% antithrombotic fibers (polyester), 3% polyurethane fabric Example 6

Test of Antithrombotic Properties

A. Introduction

In the physiological state, circulating blood circulates through blood vessels while maintaining fluidity without coagulating. This is the result of maintaining a dynamic balance between the antithrombotic properties of vascular endothelial cells and the blood coagulation and fibrinolysis systems. Platelets and blood coagulation factors are present in the blood in amounts equal to several to ten times more than the amounts required for hemostasis. Consequently, although the promoting system is dominant to the inhibiting system for the series of blood coagulation reactions, circulation is maintained as a result of being efficiently controlled dependent on endothelial cells.

This study was conducted on variations in the coagulation and fibrinolysis systems due to use of the antithrombotic bedding and sleepwear of the present invention with the understanding and cooperation of 20 subjects hospitalized for routine health examinations who were not in a thrombotic state, but rather engaged in daily lives that were closer to normal than a pre-thrombotic state.

B. Study Method

Subjects: 20 persons hospitalized for routine health examinations.

Method: The subjects were divided into a group I and a group II using the envelope method. The subjects were then allowed to nap for 2 hours starting at 2:00 PM using two types of bedding and sleepwear in the manner described below (refer to Table 1). While the subjects were asleep, the room temperature was kept at 24° C. and the subjects were prohibited from drinking starting 1 hour before napping.

Group I:
Day 1—Bedding and sleepwear of the present invention were used (antithrombotic sheets, blanket, mattress pad, pillow, shirt and trousers)
Day 2—Ordinary bedding and sleepwear were used (sheets, blanket, mattress pad, pillow, shirt and trousers)

Group II:
Day 1—Ordinary bedding and sleepwear were used
Day 2—Bedding and sleepwear of the present invention were used Components:
Filler—100% polyethylene pipes
Body case—100% cotton
Body cover—100% cotton
Other: As a result of dividing the pillow into five mesh pouches and filling them with filler, a structure results in which the location where the head is place can be finely adjusted. In addition, the five mesh pouches are adhered to the body cover, thereby resulting in a structure that supports the neck and shoulders.

TABLE 1

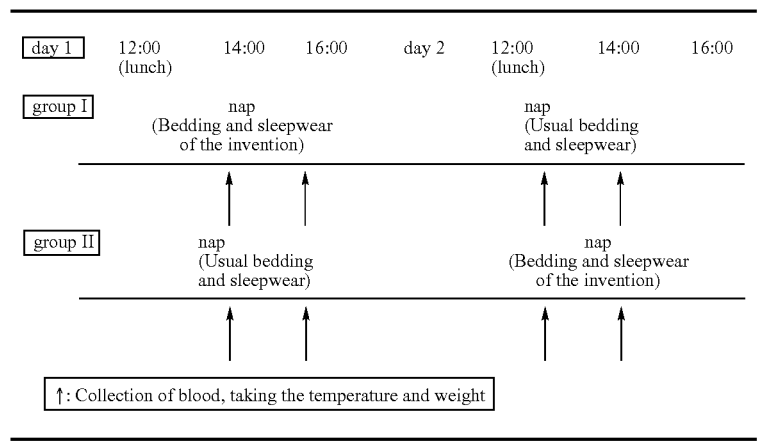

Furthermore, the following articles were used for the ordinary bedding and sleepwear.

(7) Sheets:
Form: Flat type, 150 cm wide×230 cm long
Fiber blending ratio: 100% cotton
Other: Plain fabric (100% cotton for warp and weft)

(8) Blanket
Form: Double-sided raised fibers, 140 cm wide×200 cm long
Fiber blending ratio: 100% cotton (9) Mattress Pad
Form: 90 cm wide×185 cm long×2 cm thick, weight: 1.5 kg
Fiber blending ratio:
Filling—100% cotton
Siding—100% cotton fabric
Other: Quilted

(10) Pillow
Form: Five-section filled (pipes), fine adjustable type, 60 cm wide×50 cm high (overall)

(11) Shirt
Form: Crew neck, long sleeve
Fiber blending ratio: 100% polyester fabric

(12) Trousers
Form: Long trousers
Fiber blending ratio: 100% polyester fabric Study Period: Feb. 21, 2001 to Mar. 15, 2001

C. Examined Parameters
1. Axillary body temperature, body weight
2. Whole blood viscosity, plasma viscosity, general blood test, coagulation and fibrinolysis functions
    (1) APTT, PT, HPT, TT, ATIIT, catecholamines (3 types)
    (2) P-selectin, PAI-1, β-TG, TX-B2
    (3) t-PA, NO, PGI-2, TM, MDA-LDL The parameters of 1 and 2 were measured by collecting blood samples immediately before napping and 2 hours after the start of napping. 30 ml of blood were sampled each time. The coagulation and fibrinolysis examinations performed on all subjects were conducted as shown in Table 2.

TABLE 2

| Notation Name | Examined Parameters | Standard value | Material | Unit | Measuring Method |
|---|---|---|---|---|---|
| BV | blood viscosity | 2.59–3.67 | blood | MPa · sec | Taniguchi-Ogawa's vaccum aspiration |
| PV | plasma viscosity | 1.19–1.43 | plasma | mPa · sec | Taniguchi-Ogawa's vaccum aspiration |
| adrenalin | adrenalin catecolamines (3 fractions) | not over 100 | plasma | pg/ml | |
| norad | noradrenalin catecolamines (3 fractions) | 100~450 | plasma | pg/ml | |

TABLE 2-continued

| Notation Name | Examined Parameters | Standard value | Material | Unit | Measuring Method |
|---|---|---|---|---|---|
| dopa | dopamine catecolamines (3 fractions) | not over 20 | plasma | pg/ml | |
| tPAI | Plasminogen · activator · Inhibitor (PAI-1) | not over 50 | plasma | ng/ml | |
| tp activator | tissue-type plasminogen · activator (t-PA) | not over 10 | plasma | ng/ml | |
| thrombomodulin | thrombomodulin | M2.1~4.1, F1.8~3.9 | serum | FU/ml | |
| nitrite ion | nitrite ion | not over 1 | serum | µMOL/l | |
| nitrate ion | nitrate ion | 10~71 | serum | µMOL/l | |
| MDA-LDL | MDA-LDL | | serum | U/l | |
| P-selectin | P-selectin | | plasma | ng/ml | |
| PGF1 α | 6-keto prostaglandin F1 α | not over 12 | plasma | pg/ml | |
| TX-B2 | thromboxane B2 | not over 35 | plasma | pg/ml | |
| NK | Natural Killer Cell | 18~40 | whole blood | % | |

3. Radial Artery Diameter

This was measured at arbitrary times during hospitalization.

When performing the above examinations, since measured values are easy to vary due to contamination by tissue fluid during the course of collecting blood, blood samples were collected as a general rule either by the double syringe method or by indwelling needle method.

4. Age Distribution

The following results were obtained from an analysis of age distribution by dividing the twenty subjects into ages up to 49, ages 50 to 59 and ages 60 and above.

| Age | Cases | Average Age |
|---|---|---|
| 27-49 | 8 (1) | 37.5 |
| 50-59 | 6 (3) | 54.5 |
| 60-71 | 6 (4) | 64.8 |

Figures in parentheses indicate women.

12 men, ages 27 to 65, average age: 45.1 years 8 women, ages 46 to 71, average age: 59.4 years Overall average age: 50.8 years D. Factor Analysis of Cases Since the cases in this study were hospitalized for routine health examinations, the presence of any diseases affecting their health, precautionary matters in terms of their lifestyles, required follow-up tests and an assessment of the need for treatment were performed. Since the tests performed during recent routine health examinations emphasize the existence of lifestyle diseases, the cases were examined with the emphasis on correspondingly relevant factors consisting of body weight, lipid levels, blood sugar, presence of arteriosclerotic lesions and impairment of liver function.

Points were proportionately assigned to each of the above factors as shown in Table 3, the subjects were divided into three groups consisting of normal subjects (Group A), cases with other diseases (Group B) and cases with lifestyle diseases or multiple factors thereof (Group C) according to their physical condition, and each subject was scored for each factor for Groups A, B and C. Those results are shown in Tables 4, 5 and 6.

Moreover, a control group where ordinary beddings and sleepwears were used was designated as Group K, while the where the beddings and sleepwears of the present invention were used was designated as Group PL.

Variations in blood coagulation and fibrinolysis systems were examined in Groups A, B and C that were scored and divided according to factors relating to lifestyle diseases corresponding to Groups K and PL.

As shown in Tables 4, 5 and 6, a detailed examination of the findings revealed a tendency that increased lipid levels first occurred as a deviation from the healthy state, and as lipid levels gradually increased, weight gain, arteriosclerotic lesions (which are further enhanced by smoking), diabetes and impaired liver function (primarily due to alcohol consumption) occur.

TABLE 3

Factors for lifestyle-related diseases

1. BMI (Body Mass Index)

| | | score |
|---|---|---|
| Normal | 20~40 | 0 |
| Over Weight | 24~26.4 | 1 |
| Adiposis | 26.4 and over | 2 |

2. Lipid (L) mg/dl

| Total Cholesterol (T-Ch) | | LDL | score |
|---|---|---|---|
| Normal | under 200 | under 120 | 0 |
| Borderline | 200~219 | 120~139 | 1 |
| Hypercholesterolemia | 200 and over | 140 and over | 2 |

| | Natural fat | score |
|---|---|---|
| Normal | under 150 | 0 |
| Borderline | 150~220 | 1 |
| Hypertriglyceridaemia | 220 and over | 2 |

When fatty liver is found by abdominal echo: 1 point addition

3. Blood Sugar Level (Glycemia, G) mg/dl

| | fasting | 75-OGTT 2 hours | score |
|---|---|---|---|
| Normal | under 110 | under 140 | 0 |
| Borderline | 110~126 | 140~200 | 1 |
| DM type | 126 and over | 200 and over | 2 |

4. Others

①A disorder derived from arterial scleosis (A) . . . 1 point

Hypertension or coronary arteriosclerosis which is under treatment

Having angina cordis, cardiac infarction or brain infarction as a previous disease ② Impaired liver function (H)

| | |
|---|---|
| 1. GOT, GPT, γ-GPT value not over 100 | 1 point |
| 2. GOT, GPT, γ-GPT value 100 and over | 2 points |
| 3. Rising LDH, LAP or ALP value | 1 point |
| Complication of 1 and 3 | 2 points |

TABLE 4

A group

| | | | | | | Factors | | | | |
|---|---|---|---|---|---|---|---|---|---|---|
| | Cases | | | Disease | BMI (W) | Liquid (L) | Blood Sugar (G) | Arterial Sclerosis (A) | Liver Function (H) | Total |
| 1 | O.O | M42 | | Fine | 0 | 0 | 0 | 0 | 0 | 0 |
| 2 | K.M | M37 | | Fine | 0 | 0 | 0 | 0 | 1 | 1 |
| 3 | K.K | M29 | | Fine | 0 | 0 | 0 | 0 | 0 | 0 |
| 4 | H.O | F71 | | Urine occult blood | 1 | 0 | 0 | 1 | 0 | 2 |
| 5 | K.M | M53 | | Urine occult blood | 0 | 0 | 0 | 1 | 0 | 1 |
| 6 | S.I | M49 | | Gaucoma | 0 | 2 | 0 | 1 | 0 | 3 |
| Total | | Average Age 47.5 years | | | 1 | 2 | 0 | 3 | 1 | 7 |
| | | All 20 cases in total | | | 9 | 20 | 7 | 8 | 10 | 54 |

TABLE 5

B group

| | | | | | | Factors | | | | |
|---|---|---|---|---|---|---|---|---|---|---|
| | Cases | | | Disease | BMI (W) | Liquid (L) | Blood Sugar (G) | Arterial Sclerosis (A) | Liver Function (H) | Total |
| 1 | H.I | F46 | | 1gA nephropathy | 0 | 1 + 1 | 0 | 1 | 0 | 3 |
| 2 | I.Y | M27 | | Fecal occult blood | 0 | 1 | 0 | 0 | 1 | 2 |
| 3 | S.K | F56 | | Bronchocele | 1 | 2 | 0 | 0 | 0 | 3 |
| 4 | M.A | F65 | | Gastritis | 0 | 1 | 0 | 1 | 0 | 2 |
| 5 | M.M | M35 | | Nephrolithiasis sinista | 0 | 0 | 0 | 0 | 0 | 0 |
| 6 | S.K | M62 | | Fecal occult blood | 0 | 0 | 1 | 0 | 0 | 1 |
| Total | | Average Age 43.5 years | | | 1 | 6 | 1 | 2 | 1 | 11 |
| | | All 20 cases in total | | | 9 | 20 | 7 | 8 | 10 | 54 |

TABLE 6

C group

| | | | | | | Factors | | | | |
|---|---|---|---|---|---|---|---|---|---|---|
| | Cases | | | Disease | BMI (W) | Liquid (L) | Blood Sugar (G) | Arterial Sclerosis (A) | Liver Function (H) | Total |
| 1 | S.H | M35 | | Hyperlipemia, Hepatitis | 1 | 2 + 1 | 0 | 0 | 1 | 5 |
| 2 | K.A | M65 | | Hyperlipemia, Borderline blood sugar | 0 | 2 | 1 | 0 | 0 | 3 |

TABLE 6-continued

C group

| | Cases | | Disease | BMI (W) | Liquid (L) | Blood Sugar (G) | Arterial Sclerosis (A) | Liver Function (H) | Total |
|---|---|---|---|---|---|---|---|---|---|
| 3 | T.K | M51 | Cholelithiasis, Hepatitis, Diabetes | 1 | 2 + 1 | 2 | 0 | 2 | 8 |
| 4 | H.N | M56 | Diabetes | 0 | 0 | 2 | 1 | 0 | 3 |
| 5 | A.A | F66 | Hyperlipemia, Adiposis | 2 | 2 | 0 | 1 | 0 | 5 |
| 6 | S.I | M49 | Borderline diabetes | 2 | 0 | 1 | 0 | 2 | 5 |
| 7 | S.W | F60 | Coronary arteriosclerosis | 1 | 0 | 0 | 1 | 1 | 3 |
| 8 | K.G | F58 | Hyperlipemia, Bronchocele | 0 | 2 | 0 | 0 | 2 | 4 |
| Total | Average Age 55.0 years | | | 1 | 6 | 1 | 2 | 1 | 11 |
| | All 20 cases in total | | | 9 | 20 | 7 | 8 | 10 | 54 |

E. Variations within Normal Values

The examination parameters relating to the coagulation and fibrinolysis systems excluding general blood tests, which are relating to routine health examinations, cover a diverse range of 19 types of tests.

Blood samples were collected from the members of Group K (using ordinary bedding and sleepwear) and Group PL (using the bedding and sleepwear of the present invention) before and after using the bedding and the sleepwear. With respect to the general blood tests (RBC, WBC, Hb, Ht, MCH, MCHC and PLT), the coagulation tests of TT (s, %), PT (s, %) and APTT (s, %), and electrolyte measurements (Na, K, Cl and Ca) performed before and after napping, the effects of napping resulted in changes within normal values for each Group A, B and C of Groups K and PL, and since they consisted of variations in which there were hardly any large differences, the effects of napping on the coagulation and fibrinolysis systems were examined for Groups K and PL.

Furthermore, examinations performed before napping were designated as BEFORE, while those performed after napping were designated as AFTER.

F. Examination of Cases (1) Vascular Endothelium System (Refer to Table 7)

Since vascular endothelial cells have potent anticoagulation function and a strong negative charge, they mutually repel platelets having a similar negative charge. Moreover, endothelial cells also inhibit platelet function by releasing NO (nitrogen oxide) and PGI2 (prostaglandin), and demonstrate potent antithrombotic function overall by producing and releasing TM (thrombomodulin) and t-PA (tissue plasminogen activator).

With respect to the produced amounts of t-PA, PGF1α (6-keto-prostaglandin-1α), TM, nitrite ion and nitrate ion; an roughly 10% increase was observed in Group K for PGF only after napping in a comparison of the results before and after napping of Groups K and PL, while a approximately 10% decreasing tendency was observed in Group PL. The variation range was shown within their standard values for t-PA, TM and NO.

With respect to the vascular endothelium system, the amount of PGF increased by about 10% (variation range: 5 to 15%) in Group K AFTER, while the amount of PGF tended to decrease about 10% (variation range: −7 to −27%) in Group PL AFTER.

On the basis of these findings with respect to platelet function, there was a tendency that napping in Group K AFTER had an inhibitory effect on platelets due to the increasing tendency of PGF, while napping in Group PL AFTER worked positively (thrombotropic action) on platelet function due to the decreasing tendency of PGF.

TABLE 7

| Vascular endothelium system | Group | K-A | K-B | K-C | Average | PL-A | PL-B | PL-C | Average |
|---|---|---|---|---|---|---|---|---|---|
| t-PA not over 12 mg/ml | Before | 6.0 | 6.2 | 8.2 | 7.0 | 5.5 | 6.7 | 7.8 | 6.8 |
| | After | 4.9 | 5.4 | 7.0 | 5.9 | 5.5 | 5.2 | 7.3 | 6.2 |

TABLE 7-continued

| Vascular endothelium system | Group | K-A | K-B | K-C | Average | PL-A | PL-B | PL-C | Average |
|---|---|---|---|---|---|---|---|---|---|
| PGF1 α not over 12 pg/ml | Before | 18.7 | 14.0 | 17.4 | 16.8 | 15.8 | 18.0 | 20.0 | 18.1 |
| | After | 19.8 | 16.1 | 18.3 | 18.1 | 13.0 | 13.0 | 18.6 | 16.6 |
| T.M. M2.1-4.1, F1.8-3.9 FU/ml | Before | 2.5 | 2.2 | 2.2 | 2.3 | 2.7 | 2.2 | 2.3 | 2.4 |
| | After | 2.3 | 2.1 | 2.1 | 2.2 | 2.4 | 2.2 | 2.1 | 2.25 |
| nitrite ion not over 1 μmol/l | Before | 1.1 | 1.0 | 1.1 | 1.1 | 1.3 | 1.0 | 1.3 | 1.3 |
| | After | 1.0 | 1.0 | 1.0 | 1.0 | 1.0 | 1.0 | 1.1 | 1.1 |
| nitrate ion not over 10-71 μmol/l | Before | 55.0 | 59.1 | 53.5 | 55.7 | 53.5 | 57.3 | 63.3 | 58.6 |
| | After | 56.0 | 65.8 | 51.5 | 57.2 | 57.1 | 57.5 | 63.0 | 59.6 |

(2) Platelet System (Refer to Table 8)

Variations of PAI-1, P-selectin, TX-B2 and PLT can be indicators of activation of platelet function. Platelets are normally maintained in a dormant state, while in the state in which the function of vascular endothelial cells is dominant, platelets are mutually repelled due to the negative charge of glycoproteins on the surface of vascular endothelial cells, and so the adhesion and aggregation of platelets to vascular walls is being inhibited. The variations in PAI-1, P-selectin, TX-B2 and platelet levels are shown in Table 8.

PAI-1 exhibited a decreasing tendency (variation range: −7 to −33%) of 21% on average in Group K AFTER, and exhibited an increasing tendency (variation range: −9.8 to +8.2%) of 3.1% on average in Group PL AFTER.

P-selectin exhibited an increasing tendency in Group A for Groups K and PL, and although it decreases (−23 to −18.7%) in Groups B and C for Group K, it only decreases mildly in Groups B and C for Group PL (−3 to −3.4%).

TX-B2 increased prominently in Group C for Group K, but exhibited a definite decrease in Group PL-C. Namely, although PAI-I and P-selectin exhibited minute increases and decreases throughout Groups K and PL, when platelet function is considered overall after adding TX-B2, platelet function was observed to move in the direction of a thrombogenic tendency as a result of promotion of overall platelet function in Group K AFTER, while in Group PL AFTER, since a decreasing tendency was observed for TX-B2, a hemorrhagotropic tendency is thought to have been exhibited due to inhibition of platelet function. This means that there was a decrease and inhibition of production of thromboxane A2 within platelets, and indicates sedation of the activation of platelet function resulting from the use of the antithrombotic fibers of the present invention.

TABLE 8

| Blood platelet | Group | K-A | K-B | K-C | Average | PL-A | PL-B | PL-C | Average |
|---|---|---|---|---|---|---|---|---|---|
| PAI-1 not over 50 mg/ml | Before | 41.1 | 38.3 | 42.8 | 41.0 | 36.0 | 35.5 | 42.5 | 38.5 |
| | After | 27.5 | 35.8 | 32.7 | 32.5 | 32.5 | 38.5 | 46.0 | 39.7 |
| p-selectin ng/ml | Before | 232.1 | 284.6 | 327.7 | 316.2 | 266.5 | 328.5 | 292.8 | 295.7 |
| | After | 254.0 | 265.6 | 253.0 | 257.1 | 397.0 | 325.1 | 284.3 | 285.7 |
| TX-B2 not over 35 pg/ml | Before | 25.0 | 16.8 | 70.7 | 40.9 | 22.5 | 20.3 | 50.4 | 33.0 |
| | After | 18.5 | 7.6 | 191.6 | 84.8 | 19.7 | 16.7 | 28.8 | 22.5 |
| PLT 13-36 $10^4$/μl | Before | 25.2 | 28.5 | 25.6 | 26.4 | 26.8 | 26.8 | 26.6 | 26.8 |
| | After | 24.3 | 25.5 | 24.4 | 24.7 | 25.5 | 25.8 | 24.6 | 25.2 |

(3) Coagulation System and its Related Substances (Refer to Table 9)

A comprehensive study was conducted on fibrinogen which is coagulation factor I, factor IV, $Ca^{++}$, and the thrombin controlling factors of antithrombin and MDA-LDL.

Electrolytes other than Ca (K, Na and Cl) exhibited variations that were nearly all within the physiologically normal range of no more than 1 mEq/L, and since variations in TT and HTP were also extremely small, a study in the form of table was omitted.

With respect to MDA-LDL, although mild decreases were exhibited after napping for both Groups K and PL, in the case of variations to this degree, MDA-LDL was not considered to lower the antithrombotic action of endothelial cells by inhibiting the expression of TM and t-PA by endothelial cells and enhancing the expression of tissue factor PAI-1.

With respect to PT and APTT as well, there were no well-defined variations observed in either Group K or Group PL. Since APTT was observed to exhibit an increasing tendency in Group K and mild decreasing tendency in Group PL, the intrinsic coagulation reaction system was observed to tend to be mildly prolonged after napping in Group PL as compared with Group K.

ing in increased hematocrit values when the rise in body temperature was accompanied by perspiration, increases in whole blood viscosity were observed. Moreover, when a tendency towards hypersecretion of catecholamines was observed, increases in RBC and WBC counts as well as activation of platelet function were observed due to the constrictive action on blood vessels within the spleen. Moreover, together with activation of the coagulation system, increases in whole blood viscosity and plasma viscosity were also predicted. In actuality, as shown in Table 10, decreasing tendencies were observed as a result of napping for variations in whole blood viscosity, plasma viscosity and Ht values in all of the AFTER cases for both Groups K and PL.

Among the three types of catecholamines, the most interesting was the variation in the level of noradrenaline. Although noradrenaline levels were elevated to the vicinity of the upper limit in all BEFORE cases for both Groups K and PL, in the AFTER cases, noradrenaline levels had similarly decreased to the level of 45-55% on average for both Groups K and PL. Since the stimulatory action on sympathetic nerve

TABLE 9

| Coagulation associated | Group | K-A | K-B | K-C | Average | PL-A | PL-B | PL-C | Average |
|---|---|---|---|---|---|---|---|---|---|
| Fib. | Before | 10.4 | 12.0 | 9.8 | 10.7 | 10.7 | 11.8 | 9.8 | 10.7 |
| sec | After | 11.0 | 12.6 | 10.4 | 11.3 | 11.1 | 12.5 | 10.4 | 11.3 |
| Fib. | Before | 242.6 | 218.6 | 262.3 | 243.4 | 239.6 | 220.3 | 266.1 | 244.5 |
| 200-400 mg/dl | After | 228.3 | 205.0 | 227.8 | 227.8 | 227.5 | 206.1 | 245.6 | 228.4 |
| AT3 | Before | 108.3 | 112.0 | 102.1 | 107.0 | 107.8 | 110.0 | 99.7 | 105.2 |
| 80-120% | After | 101.0 | 103.0 | 93.7 | 98.7 | 100.6 | 103.3 | 93.1 | 98.5 |
| Ca | Before | 9.1 | 9.8 | 9.0 | 9.1 | 8.9 | 9.2 | 9.0 | 9.1 |
| 8.2-10.8 mEg/l | After | 9.0 | 8.9 | 8.9 | 9.0 | 8.9 | 8.9 | 8.6 | 8.8 |
| MDA-LDL | Before | 111.5 | 145.0 | 127.1 | 127.8 | 111.7 | 130.8 | 135.6 | 127.0 |
| U/l | After | 102.3 | 116.1 | 110.4 | 109.7 | 99.8 | 114.2 | 110.4 | 108.4 |
| PT | Before | 106.5 | 121.1 | 116.0 | 114.7 | 107.8 | 118.0 | 116.2 | 114.2 |
| % (sec) |  | (11.4) | (10.9) | (11.1) | (11.2) | (11.4) | (11.0) | (11.1) | (11.2) |
|  | After | 108.1 | 119.0 | 113.7 | 113.6 | 106.7 | 121.5 | 115.7 | 114.8 |
|  |  | (11.4) | (11.1) | (11.2) | (11.2) | (11.4) | (10.9) | (11.1) | (11.2) |
| APTT | Before | 88.7 | 132.8 | 120.3 | 114.7 | 94.0 | 73.7 | 111.3 | 96.0 |
| % (sec) |  | (30.1) | (30.6) | (30.3) | (30.4) | (29.6) | (29.7) | (29.8) | (29.8) |
|  | After | 85.1 | 150.4 | 140.1 | 126.8 | 82.1 | 80.2 | 108.6 | 92.8 |
|  |  | (30.5) | (30.8) | (30.7) | (30.7) | (30.4) | (29.7) | (30.2) | (30.1) |

(4) Other Factors, BV, PV and CA (Catecholamines) (Refer to Table 10)

Rises in body temperature were observed due to the effects of napping, and since the blood became concentrated resulting receptors decreases due to the reduction by half in noradrenaline levels, decreased circulating blood volume due to a reduction in peripheral vascular resistance, and decreased BV and PV due to reduced blood flow rate were observed.

TABLE 10

| Others | Group | K-A | K-B | K-C | Average | PL-A | PL-B | PL-C | Average |
|---|---|---|---|---|---|---|---|---|---|
| BV | Before | 3.27 | 3.29 | 3.41 | 3.33 | 3.34 | 3.18 | 3.38 | 3.31 |
| 2.59-3.67 mPa · sec | After | 3.13 | 3.06 | 3.16 | 3.12 | 3.17 | 3.03 | 3.24 | 3.15 |
| PV | Before | 1.44 | 1.41 | 1.51 | 1.46 | 1.43 | 1.50 | 1.46 | 1.46 |
| 1.19-1.43 mPa · sec | After | 1.40 | 1.43 | 1.41 | 1.41 | 1.31 | 1.41 | 1.44 | 1.39 |
| adrenalin | Before | 38.5 | 38.8 | 39.8 | 39.2 | 34.8 | 42.0 | 39.0 | 38.8 |
| not over 100 pg/ml | After | 19.0 | 33.6 | 25.7 | 26.2 | 34.6 | 35.8 | 25.3 | 31.3 |
| noradrenalin | Before | 483.8 | 422.6 | 562.1 | 496.8 | 468.5 | 414.5 | 652.1 | 525.8 |
| 100-450 pg/ml | After | 223.1 | 236.3 | 257.0 | 240.7 | 248.0 | 229.6 | 296.3 | 261.9 |
| dopamin | Before | 15.5 | 20.3 | 26.1 | 21.2 | 15.0 | 19.0 | 25.7 | 20.5 |
| not over 20 pg/ml | After | 14.8 | 15.5 | 22.3 | 18.1 | 14.1 | 16.0 | 14.0 | 14.7 |
| Ht % | Before | 41.2 | 41.7 | 42.7 | 42.0 | 42.0 | 40.6 | 42.6 | 41.8 |
|  | After | 40.2 | 39.5 | 40.6 | 40.2 | 40.7 | 39.2 | 40.7 | 40.3 |

G. Discussion

Since variations in PAI-1, P-selectin and TX-B2are of interest with respect to those factors involved in the coagulation and fibrinolysis systems, and discussion is provided regarding those factors.

1. PAI-1 and P-selectin

PAI-1 is produced in vascular endothelial cells, vascular smooth muscle cells and fat cells, and is the main inhibitory factor of t-PA. PAI-1 is also present in platelets, and is released accompanying platelet aggregation. The PAI-1 derived from platelets is mainly released at the sites of thrombi, and irreversibly binds to fibrin to exist in a concentrated form around fibrin to neutralize the activity of t-PA.

Although PAI-1 exhibited a decreasing tendency in Groups A, B and C of the control group (Group K), it exhibited a somewhat increasing tendency in Groups B and C of Group PL.

In the study of t-PA shown in Table 7, t-PA exhibited a decreasing tendency after napping common to both Groups K and PL, and since an increasing tendency was not observed in the consumption of t-PA, a tentative state of equilibrium was thought to exist with the variations in PAI-1. Moreover, in the case of P-selectin, although decreasing tendencies were prominent in Group C of Group K, the decreases were only slight in, Group C of Group PL.

These findings indicate that, with respect to the formation of PAI-1 and P-selectin, prominent decreases did not occur in Group PL and compared with Group K for those subjects in Group C (subjects with lifestyle diseases). Namely, this indicates that among the subjects in Group C, although decreased platelet function was observed in Group K, there was no such decrease observed in Group PL or the decrease was only extremely mild. Overall platelet function is thought to have been inhibited considerably in Group C AFTER for Group PL as will be described with respect to the variations in TX-B2.

2. TX-B2

Platelets have a positive feedback pathway that promotes activation of surrounding platelets, in which pathway they produce the potent platelet activating substance TX-A2 when platelets are activated. However, TX-A2 is an extremely unstable substance that has a half-life of about 20 seconds, after which it is broken down to TX-B2. Changes in the levels of TX-B2 indicate the activation state of platelet function.

TX-B2 exhibited decreasing tendencies after napping in. Groups A and B of Group K and in Groups A and B of Group PL. In contrast, despite exhibiting a prominent increasing tendency after napping in Group C of Group K, it exhibited a remarkable decreasing tendency in Group C AFTER of Group PL.

These findings indicate that, in cases afflicted with lifestyle diseases, elevation of body temperature following the use of ordinary bedding activates platelet function resulting in the observance of a remarkable increase in TX-B2 and closely approaching a pre-thrombotic state. In Group PL (consisting of subjects that used the bedding and sleepwear of the present invention), inhibition of increases in TX-B2 mean that activation of platelet function decreased, and indicates the pre-thrombotic state was abated.

These prominent formation and decreasing tendencies of TX-B2 in Group C of Group PL are thought to indicate action that resembles that of anti-inflammatory agents and analgesics such as aspirin and indometacin which inhibit the enzyme activities of enzymes such as cyclooxygenase and phosphorylase A2 that are involved in TX-A2 synthesis pathway.

3. Thrombin Control Mechanism

The biological denaturants, glycated proteins (AGE), and the acid denatured LDL, inhibit the expression functions of TM and t-PA, while conversely are said to lower the antithrombotic action of endothelial cells by enhancing the expression of tissue factor PAI-1. In looking at the variations in MDA-LDL due to napping shown in Table 9, since MDA-LDL levels decreased on average by 14.2% in Group K and by 14.7% in Group PL, the antithrombotic action of endothelial cells was maintained due to the weakened inhibition of the TM and t-PA expression functions of endothelial cells.

Moreover, in looking at the variations in TM and t-PA according to Table 7, TM levels hardly changed at all, while t-PA decreased on average by 15.8% in Group K and by 8.9% in Group PL, thus indicating that Group PL exhibited a smaller decrease in the antithrombotic function of endothelial cells. Moreover, according to Table 9, there were no large variations in ATIII as shown below.

Group K: Fibrinogen level: Down 6.5% on average, 0.6second delay

Group PL: Fibrinogen level: Down 6.6% on average, 35 0.6 second delay

As shown in Table 9, ATIII levels decreased by 7.8% on average in Group K and by 6.4% on average in Group PL. Since ATIII is normally present in considerable excess with respect to the amount of thrombin formed, these degrees of decreases can be adequately dealt with in terms of the amount of thrombin formed. Consequently, the formed thrombin is bound by fibrinogen, TM (thrombomodulin) and ATTIII, and its activity is controlled. Namely, the thrombin control function is judged to be functioning well. On the basis of this finding, in consideration of variations in LDL, t-PA, TM and ATIII overall, the antithrombotic properties of vascular endothelial cells are thought to be maintained between in Group PL than in Group

H. Summary

A study was conducted on changes in the blood coagulation and fibrinolysis systems caused by napping using the bedding and sleepwear of the present invention.

With respect to the function of the vascular endothelium system, the variations in the levels of t-PA, TM and NO were small, while only PGF increased in Group K (inhibiting platelet function) and exhibiting a decreasing tendency in Group PL (promoting platelet function). With respect to platelet function, variations in TX-B2 were extremely characteristic, exhibiting an increasing tendency in Group C AFTER in Group K in which lifestyle diseases were observed, while exhibiting a clear decreasing tendency in Group C of Group PL.

Even when considering the variations in PGF, overall platelet function was affective positively (thrombotropic action) in Group K AFTER, and was affected negatively (antithrombotic action, or hemorrhagotropic action) in Group PL AFTER. Furthermore, the thrombin inhibitory mechanism was effectively maintained by fibrinogen, TM and ATIII.

With respect to catecholamines, although the levels of noradrenaline in particular exhibited values approaching the upper limit levels in Group K BEFORE and Group PL BEFORE, since they decreased by half AFTER, decreasing tendencies were observed for BV and PV due to decreased a receptor action.

It is interesting to note that the increase in TX-B2 of Group K AFTER in Group C and conversely the prominent decrease in TX-B2 in Group PL AFTER combined with the decrease in PGF in Group PL AFTER are thought to represent the same phenomenon as the so-called aspirin dilemma. Namely, with respect to the inhibition of the enzymatic action of cyclooxygenase in platelets and vascular endothelium caused by the action of the composition of the present invention, the promotion of antithrombotic action caused by a decrease in TX-B2. is thought to be quite significant due to the production of TX-B2 being strongly inhibited in Group C AFTER of Group PL as shown in Table 8, and the thrombotic tendency caused by decreased PDF resulting from the mild decrease in PGF production. Thus, in overall terms, the tendencies associated with the antithrombotic action of the composition of the present invention observed following napping were determined to constitute action dominated by antithrombotic properties without a hemorrhagic tendency becoming dominant in the same manner as that which occurs when using a small amount of aspirin.

Example 7

Negative Ion Releasing Effect and Antimicrobial Activity of Antithrombotic Composition of Present Invention The antithrombotic composition of the present invention is a kind of ceramics which absorbs and resonates the minute amounts of vegetative light rays released from the body (equivalent to 5-15 microns) and amplifies them 1.2-1.5.times to radiate new vegetative light rays. Namely, together with exhibiting far infrared effects, since the penetrating ability of the radiated energy is proportional to the square root of the wavelength, and penetrating ability increases the longer the wavelength, the composition of the present invention enhances the energy penetrating effect and negative ion (OH$^-$) effect due to the action of amplifying and radiating absorbed energy and the action of molecular translation.

The efficient release of negative ions from fibers containing the composition of the present invention has been clearly determined and verified by combustion tests (in compliance with the Oxygen Index Method of JIS K7201) (refer to Table 11).

Here, filters consisting of 100% fibers (polyester) containing the composition (Example 2) of the present invention and 100% ordinary polyester fibers (normal filter) were produced for use as samples, a mixed gas of oxygen and nitrogen was passed through the filters, xylene was burned and the minimum oxygen concentrations at those times were measured.

TABLE 11

| Sample | | Antithrombogenic filter | Normal filter |
|---|---|---|---|
| burning test (Oxygen Index method based on JIS K7201) | | | |
| Oxigen | 1 round | 17.3 | 17.7 |
| Index | 2 round | 17.3 | 17.6 |
| | 3 round | 17.4 | 17.6 |
| | Average | 17.3 | 17.6 |
| burning | 1 round | 105 | 105 |
| hour | 2 round | 95 | 96 |
| (second) | 3 round | 98 | 105 |
| | Average | 99 | 102 |
| Burning conditions under 0.1% low oxygen concentration from a given oxygen index | | | |
| | 1 round | a little remained to be burnt | not burn |
| | 2 round | a little remained to be burnt | not burn |
| | 3 round | a little remained to be burnt | not burn |

In addition, fibers containing the antithrombotic composition of the present invention also passed the strict antimicrobial effect tests defined by the FDA (United States Food and Drug Administration) and AATCC (American Association of Textile Chemists and Colorists) (refer to Table 12).

Furthermore, antimicrobial effect tests were conducted by inoculating Petri dishes with *Staphylococcus aureus* and *Klebsiella pneumoniae* and measuring the number of bacteria immediately after and 24 hours after inoculation with antithrombotic fibers of the present invention and polyester fibers (control).

TABLE 12

Anti bacterial test
test method: FDA U.S. Pharmacopoeia 23 Microbial Limit Test (61)

| | Test Results | Limit |
|---|---|---|
| General viable cell count (CFU/g) | $1.0 \times 10$ | — |
| E. Coli | negative | negative |
| Staphylococcus aureus | negative | negative |
| Salmonella | negative | negative |
| Pseudormonas aeruginosa | negative | negative |
| Fungus (CFU/g) | <10 | <10 |
| Yeast (CFU/g) | <10 | <10 |

Anti bacterial test
test method: AATCC 100-1999 Antibacterial Finishes on Textile Materials

| | immedeately after inoculation (CFU/g) | 24 hours after inoculation (CFU/g) | Sterile rate (%) |
|---|---|---|---|
| *Staphylococcus aureus* | | | |
| Control | $1.9 \times 10^5$ | $1.0 \times 10^2$ | — |
| Antithrombotic fiber | $1.9 \times 10^5$ | 0 | >99.99 |
| Pheumobacillus | | | |
| Control | $2.0 \times 10^5$ | $2.8 \times 10^5$ | — |
| Antithrombotic fiber | $2.0 \times 10^5$ | $1.9 \times 10^4$ | 90.50 |

Accordingly, fibers containing the composition of the present invention are also worthy of attention as fibers capable of preventing nosocomial infections and domestic infections.

Industrial Applicability

The composition of the present invention as well as bedding, sleepwear and other articles containing the same are capable of allowing antithrombotic properties to be dominant without allowing the occurrence of a hemorrhagic tendency.

What is claimed is:

1. A method for decreasing the production of TX-B2 in a person in need thereof comprising disposing in or on an article an effective antithrombotic amount of a composition and providing the article to be in close proximity to the skin of the person for a time of 2 hours or more, the composition comprising (i) alumina, (ii) at least one substance selected from the group consisting of silica and titanium oxide, (iii) at least one element or compound selected from the group consisting of platinum, a platinum compound, palladium, a palladium compound, iridium, an iridium compound, rhodium and a rhodium compound and (iv) at least one element or compound selected from the group consisting of silver, a silver compound, gold and a gold compound.

2. The method according to claim 1, wherein said alumina (i) is in an amount of 20 to 60 parts by weight; said at least one substance (ii) is in amount of 40 to 80 parts by weight and said at least one element or compound (iii) is in an amount of 0.0005 to 0.10 parts by weight.

3. The method according to claim 1, wherein said alumina (i) is in an amount of 30 to 50 parts by weight and has a particle diameter of 2 μm or less; said at least one substance (ii) is 50 to 70 parts by weight; and said at least one element or compound (iii) is in an amount of 0.001 to 0.004 parts by weight.

4. The method according to claim 1, wherein said at least one element or compound (iv) is in an amount of 0.5 to 5 parts by weight.

5. The method according to claim 1, wherein said at least one element or compound (iv) is in an amount of 0.7 to 2.0 parts by weight.

6. The method according to claim 1, wherein the article is selected from the group consisting of underpants, tights, stockings, hosiery, pajamas, a sleeping robe, a negligee, a sweater, a shirt, trousers, a skirt, a blouse, a kimono, a vest, an apron, a futon, a futon cover, a blanket, a sheet for bedding, a mattress pad, a pillow, a pillow cover, a mattress, socks, a hat, a necktie, a handkerchief, a waist band, shoes, carpeting, a curtain, a bed and a chair.

7. The method according to claim 1, wherein 0.1 to 25% by weight of said composition is contained in bedding or sleepwear.

8. The method according to claim 1, wherein 0.1 to 3% by weight of said composition is contained in bedding or sleepwear.

\* \* \* \* \*